Nov. 8, 1966 F. C. TOMLINSON Plant Pat. 2,684
PYRACANTHA PLANT
Filed Dec. 30, 1964
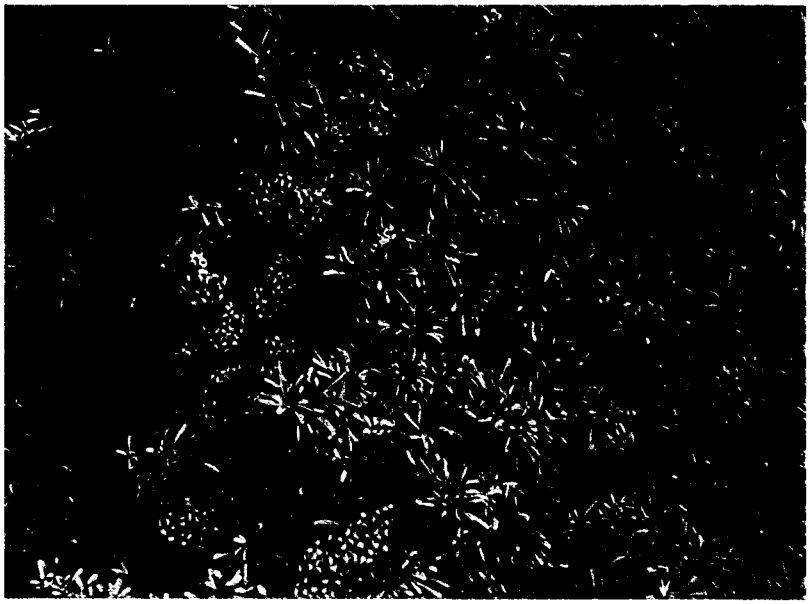
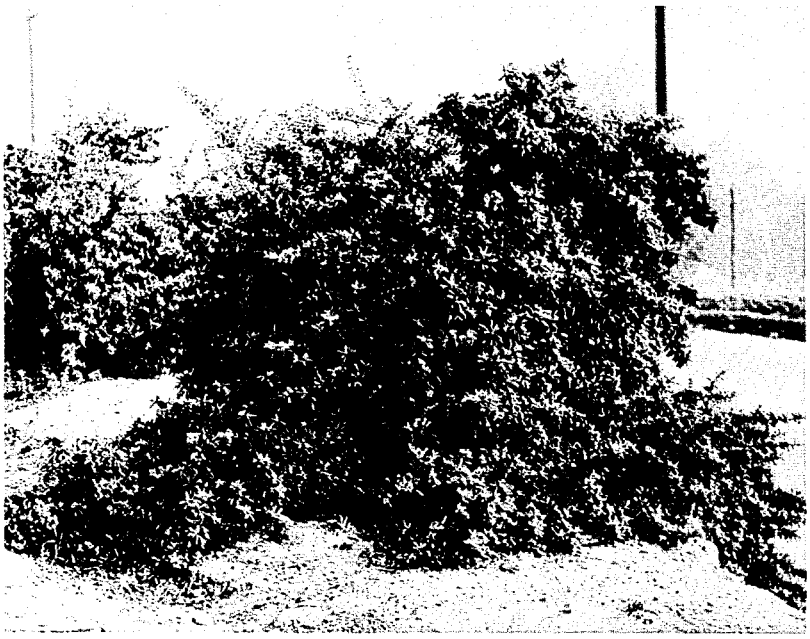
INVENTOR
FRANCIS C. TOMLINSON
BY J. F. Cumes
ATTORNEY United States Patent Office Plant Pat. 2,684
Patented Nov. 8, 1966

2,684
PYRACANTHA PLANT

Francis C. Tomlinson, 524 N. Painter, Whittier, Calif.

Filed Dec. 30, 1964, Ser. No. 422,475
1 Claim. (Cl. Plt.—54)

This invention relates to a new and distinct variety of Pyracantha plant having particularly attractive features as an ornamental shrub and in particular to a new Pyracantha plant characterized by its dwarfed, compact growth which attains not more than thirty-one inches in height, its small leaves and abundance of orange red berries.

The small size of the plant coupled with the fact that this plant produces a profusion of bright colored berries borne in heavy verticillate clusters make it particularly desirable for landscaping properties that have limited garden area.

The plant was discovered by me growing as a chance seedling on my property located at 524 Painter, in the city of Whittier, county of Los Angeles, State of California in the year 1953. The plant was found growing in a cultivated bed of *Pyracantha fortuneana* sometimes called *Pyracantha crenato-serrata*. The plant has been grown in the coastal region of southern California and has been experimentally planted in regions that are subject to colder weather. From experiment it has been found that the plant of the new variety can be exposed to temperatures that drop as low as 25 degrees F. but will not withstand any temperature below that point without suffering damage. The profusion of berries borne by so small a plant make it particularly attractive during the winter months.

The new variety distinguishes from its seed parent *Pyracantha fortuneana* in that it is very much smaller in size as a plant and the size of the leaves are also much smaller. The plant is slower growing than its seed parent and it takes approximately six years to reach a height of thirty-one inches, which appears to be the maximum growth since the initial plant has not grown any taller in eleven years. The plant forms a compact bush that is substantially upright and spreading and is practically thornless, the few thorns it has are relatively far apart and are usually very small.

The accompanying illustrations in full color show a full grown plant and a close-up view of a cluster of berries and leaves. The colors are as close as can be reproduced by the process employed.

The new variety of Pyracantha has been reproduced asexually in my growing grounds by means of cuttings, and the distinguishing characteristics of the new variety are evident in the resulting plants and the new variety appears to be well established. The new variety cannot be reproduced true from seed.

In the following description of the plant, bloom and berries, the color names and numbers used in describing the leaves and berries are based on the nomenclature used in the Horticultural Colour Charts adopted by the British Colour Council.

*The plant*

Form: A vigorous, compact substantially upright and spreading shrub that has the habit of developing several main stems arising from the ground.

Growth habit: The plant is a slow growing bush that normally requires approximately six years to attain a height of thirty-one inches and a spread at some places of about four feet.

Foliage:

*Amount.*—Very heavy.

*Size.*—Leaves are one and one eighth inches in length and vary from one-quarter to five-sixteenths of an inch in width.

*Color.*—Upper surface is Spinach Green 0960. Under side is Lavender Green 000761.

*Shape.*—The leaves are substantially oblong-obovate with the apex of a few of the leaves being slightly emarginate while the apex of the majority of the leaves is obtuse; the base of the leaves is cuneate with the length of the taper being relatively long; the margin of the leaves is entire. The upper surface of the leaves is substantially glabrous while the bottom surface of the leaves is slightly tomentose; this being particularly true regarding the midrib.

*Veins.*—The veins are extremely faint and the arrangement of these veins is alternate.

*Arrangement.*—The leaves form in groups up to seven or eight leaves and extend from a common node attached to the branch. The arrangement of the leaves of a group could be described as whorled.

*Stems.*—The stems of the plant are generally slender and are covered with a rust-colored pubescence that is particularly noticeable on the new growth. Color—the stems are dark brown and the majority of the stems can be described as short for a Pyracantha.

Thorns: The plant has very few thorns and these are usually one-quarter of an inch in length; occasionally a thorn may reach a length of one-half inch.

*The bloom*

Blooming period: The plant blooms usually in March and April in southern California where weather conditions vary considerably from year to year.

Arrangement: The blooms are borne in profusion and form clusters on the laterals.

Buds: The buds are attached to short peduncles and appear in large clusters that vary considerably in number. Size—the buds are quite small and vary in size between 1/16" and 1/8".

Flowers:

*Arrangements.*—The flowers appear in large clusters and several clusters are grouped together.

*Calyx.*—The calyx is light green in color and varies from 1/16" to 1/8" in size.

*Petals.*—The petals are arranged in groups of five to form a five pointed star. Size—the individual petals are up to 1/8" in length and the overall dimension of the five pointed star is usually 5/16" in diameter. Color—the petals are white.

*Stamens.*—Each flower has approximately 20 stamens and the color of the stamens is lemon yellow.

*The berries*

Texture: The berries are substantially pithy but not dry.

Size: The berries vary from 5/16" to 3/8" in size.

Shape: The upper and lower ends of the berries are definitely flattened.

Color:

*When first becoming colored.*—When first becoming orange red the color is Vermillion 18.

*When mature.*—The color of the mature berries is approximately Signal Red 719/1.

Arrangement: The berries form in verticillate clusters around their stem and the size of the cluster is roughly one and one-half inches in diameter and generally about two and one-half inches in length.

Persistence: The berries remain on the bush throughout the winter.

Ripening period: The berries begin to ripen in October but do not turn their brightest orange red until late November or early December. The color becomes slightly darker red as the berries reach their maximum ripeness.

Having described my invention, I claim:

The new and distinct variety of Pyracantha plant substantially as shown and described herein, characterized especially by its very dwarfed compact, substantially upright and spreading growth habit, its small leaves, its slow growing habit, and by the small number of thorns.

References Cited by the Examiner

UNITED STATES PATENTS

P.P. 884 10/1949 Sawada ---------- 54

OTHER REFERENCES

Wholesale Catalog for 1959–1960, Monrovia Nursery Co., p. 68.

ABRAHAM G. STONE, *Primary Examiner.*

R. E. BAGWILL, *Assistant Examiner.*